United States Patent [19]

Bambara et al.

[11] Patent Number: 4,790,190
[45] Date of Patent: Dec. 13, 1988

[54] ON-LINE ACOUSTIC DETECTION OF BEARING DEFECTS

[75] Inventors: Joseph E. Bambara, North Babylon; John L. Frarey; Richard L. Smith, both of Latham, all of N.Y.

[73] Assignee: Servo Corporation of America, Hicksville, N.Y.

[21] Appl. No.: 104,801

[22] Filed: Oct. 2, 1987

[51] Int. Cl.$^4$ ............................................. G01N 29/04
[52] U.S. Cl. ..................................... 73/660; 246/169 S
[58] Field of Search ............ 246/169 S, 169 D, 169 A, 246/169 R; 73/593, 660, 587

[56] References Cited

U.S. PATENT DOCUMENTS

| | | | |
|---|---|---|---|
| 3,016,457 | 1/1962 | Brown et al. | 73/593 |
| 3,163,384 | 12/1964 | McCauley | 246/169 S |
| 4,129,276 | 12/1978 | Svet | 246/169 S |
| 4,696,446 | 9/1987 | Mochizuki et al. | 246/169 S |

FOREIGN PATENT DOCUMENTS 151237 11/1980 Japan ..................................... 73/660

*Primary Examiner*—Stewart J. Levy
*Assistant Examiner*—Louis M. Arana
*Attorney, Agent, or Firm*—Kane, Dalsimer, Sullivan, Kurucz, Levy, Eisele & Richard

[57] ABSTRACT

This invention relates to apparatus for the detection of accustic impact frequencies, characteristic of bearing assembly failure during operation, which modulate an acoustic carrier frequency band. This apparatus allows for on-site or field application with high-level of ambient noise such as are present in railroad yards. This apparatus allows for early detection of such failures, so that a repair may be made before damaging heat build-up or catastrophic bearing failure occurs. Additionally, with sufficient early warning in railroad applications, a train may continue running to a railyard for convenient shop repair rather than expensive field repair.

16 Claims, 3 Drawing Sheets

ON-LINE ACOUSTIC DETECTION OF BEARING DEFECTS

BACKGROUND OF INVENTION

1. Field of Invention

The present invention relates to bearing defect detectors and in particular to an acoustic system for detecting defects in the bearings of moving railroad cars.

2. Description of the Prior Art

Heretofore, the detection of defects in railway car bearing has relied upon stationary infrared sensing means along railroad tracks to detect an abnormal heat rise associated with bearing failure in passing railroad cars. While such systems have enjoyed widespread use and an industry-wide reputation for reliability, they suffer from a serious drawback in that they detect a defect only after a damaging heat build-up has occurred within the bearing. Furthermore, this heat build-up often does not occur until a total bearing failure is eminent, thereby normally warranting an immediate stopping of the train so that an emergency field repair may be done. As this requires a delay in the train until a repair team may arrive with the necessary equipment, the total cost of this procedure can be very high.

It is known that defects in tapered roller bearings, such as those used in railroad cars, produce sounds, during operation, at characteristic frequencies dependent upon the location or type of defect (i.e., at the bearing cup, cone, or roller), the combination of the size of the wheel and the bearing capacity (frequently encountered combinations on railroads are a 28 inch wheel with a 70 ton capacity bearing, a 33 inch wheel with a 70 ton capacity bearing, a 36 inch wheel with a 70 ton capacity bearing, and a 36 inch wheel with a 100 ton capacity bearing), and the speed of the train (which, of course, for a given diameter of the wheel, is proportional to the rotational frequency of the wheel). Additionally, irregularities in the wheel circumference ("flats") produce a characteristic frequency dependent upon rotational frequency of the wheel.

Thus, for any given train speed, a defective bearing will produce a sound at one of twelve characteristic frequencies dependent upon the location of the defect and the combination of the train speed, wheel size and bearing capacity. Ideally, one need only listen for the sounds of a passing train to try to detect the characteristic sound frequencies to determine the condition of the bearings of the passing train. Unfortunately, railroad trains operate in extremely noisy environments. Train noises (such as wheel/rail rubbing, flange/rail squeal, loose equipment and cargo sounds, car-body noises, and clacking of rail joints for track circuits) and wind "swish" are low-frequency sounds which tend to camouflage the impact frequencies produced by a defective bearing. Thus, while the production of characteristic impact frequencies in a moving bearing have been known, it has heretofore been impossible to isolate the impact frequencies in a meaningful manner so as to provide useful and reliable information.

OBJECTS AND SUMMARY OF INVENTION

It is therefore an object of this invention to detect a defective bearing, particularly in on-site railroad applications, before damaging heat build-up has occurred thereby giving repair crews sufficient early warning so as to allow the train to safely run to a place where repairs can be conveniently and inexpensively performed and/or to repair the bearing in its early stages of failure.

It is a further object of this invention to analyze, before repairs begin, the type of bearing defect (i.e., whether the defect is in the bearing cup, cone, or roller) which has occurred.

It is a further object of this invention to detect these defects reliably in a noisy environment such as is common in railroad and other industrial application.

In analyzing the sounds generated by passing railroad trains, the Applicants have found that the impact frequencies characteristic of various bearing defects are generated in amplitude-modulated form on an acoustic carrier frequency band which is independent of the speed of the passing train.

Therefore, apparatus which includes a microphone is placed beside railroad tracks so as to monitor the sounds emanating from the wheels and bearings of a passing railroad train. A series of electronic amplifiers and preliminary filters is used to increase the output of the microphone to a usable voltage level and to filter extraneous frequencies from the resulting electronic signal. This allows the apparatus to operate effectively notwithstanding excessive ambient noise.

After electronic amplification and preliminary filtering, the signal consists predominantly of the preselected carrier frequency band which, in the presence of the characteristic impact frequencies of bearing defects, will be generated within an envelope of the characteristic impact frequencies. In other words, there is an amplitude-modulated signal with a preselected carrier frequency band within an envelope defined by any characteristic impact frequencies which may be present.

Standard amplitude demodulation techniques are used to extract the envelope in which the carrier frequency band is being transmitted.

The extracted frequency signal is processed by a low-frequency bandpass filter which passes only the frequency range in which the various characteristic impact frequencies occur.

A spectral analysis of the resulting signal is performed. The predominant frequency values of the spectral analysis are compared to the expected characteristic impact frequency values.

This comparison may be done manually, but is preferably automated with the output of a railroad train speed sensor used to generate the expected values of characteristic impact frequencies.

When a match between the predominant frequency values of the spectral analysis and the expected characteristic impact frequency value is found, the operators of the apparatus notify the operators of the train in order that appropriate plans for repair may be made.

BRIEF DESCRIPTION OF THE DRAWINGS

Further objects and advantages of the invention will become apparent from the following description and claims wherein:

DETAILED DESCRIPTION OF THE PREFERRED EMBODIMENT

Figure 1:
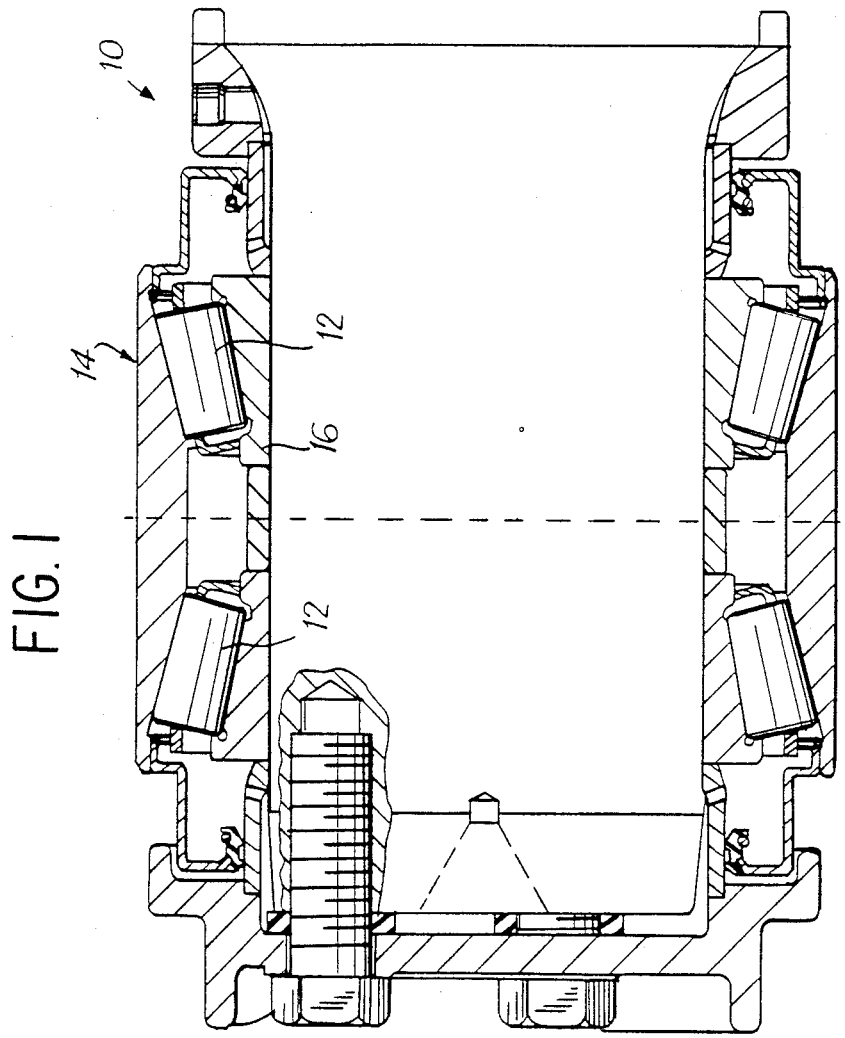
FIG. 1 shows a view in elevation of a typical tapered bearing as is used in railroad applications.

Referring now to the drawings in detail, FIG. 1 shows a tapered roller bearing assembly 10 such as those commonly used in railroad applications. Components which commonly fail are the roller 12, the cup 14 and the cone 16. Upon failure of any component, a characteristic component-dependent rotational speed-dependent acoustic impact frequency generates a sound spectrum which amplitude modulates a carrier acoustic signal of rotational speed-independent frequency contained within said spectrum.

It has been found that the carrier signal has a frequency of approximately 10-12 kilohertz, while sample characteristic impact frequencies for a 6½"×12" bearing assembly (100 ton capacity with a 36" wheel) are listed below:

| Characteristic Impact Frequencies (Hz) | | | |
| --- | --- | --- | --- |
| | 20 mph | 30 mph | 40 mph |
| 36 inch wheel 6 ½" × 12" assembly (100 ton capacity) | | | |
| roller | 14.6 | 21.9 | 29.1 |
| cup | 32.0 | 48.0 | 64.0 |
| cone | 39.4 | 59.1 | 78.9 |

It should be noted that wheel irregularities ("flats") produce a characteristic acoustic frequency which does not modulate the aforementioned carrier frequency band. However, as this system is acoustic in nature, parallel circuitry for the detection of "flats" may be easily added.

Figure 2:
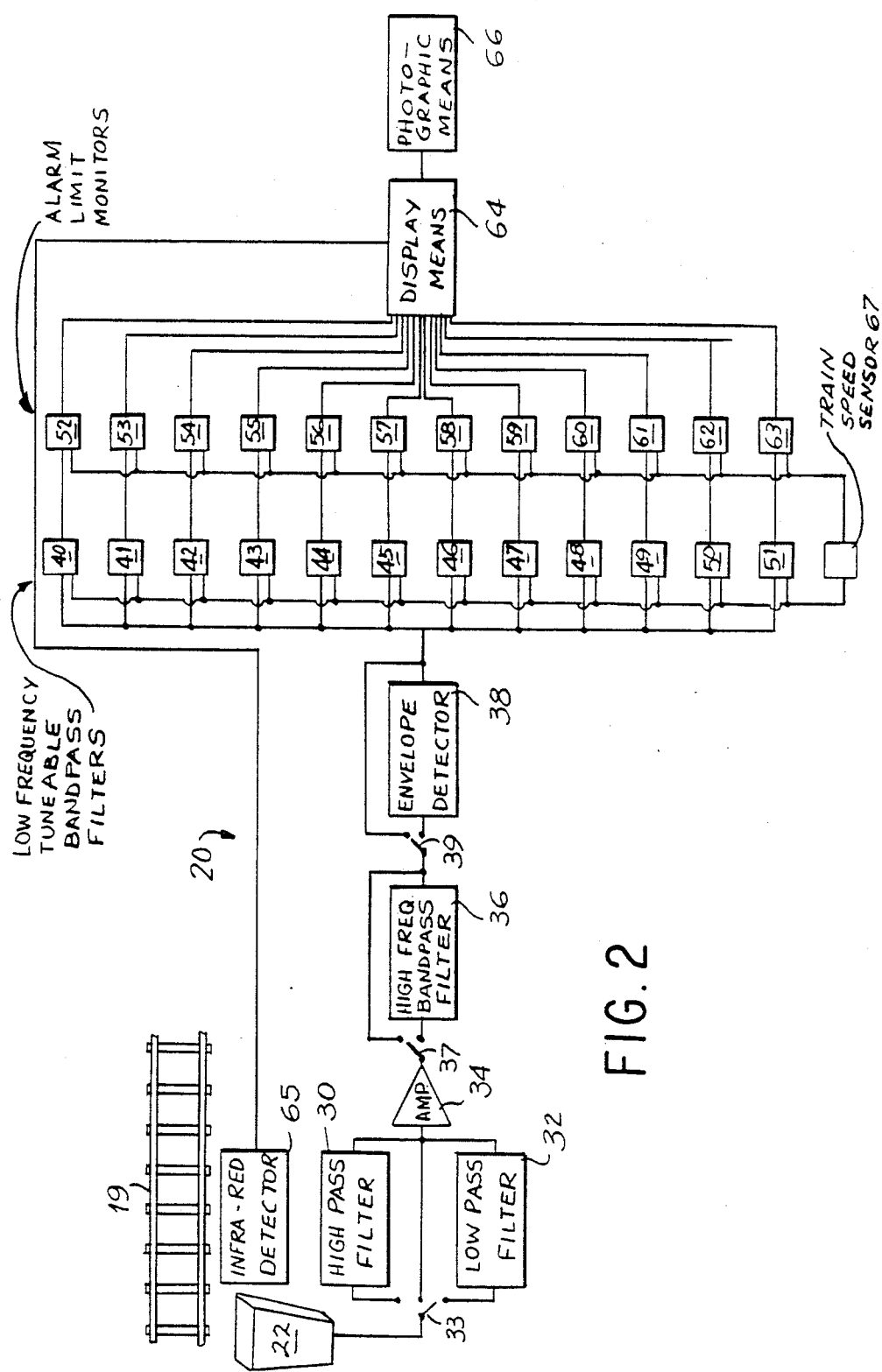
FIG. 2 shows a schematic of the acoustic bearing defect detector apparatus of the present invention.

Referring now to FIG. 2 wherein the vibration envelope detector 20 is shown, input is received from a source 22 electrical signal. Ideally, for on-site applications, this is a an electret microphone in a horn assembly with a cavity optimized for the desired bandpass of 10 to 12 kilohertz. A horn is desired as it provides the directional characteristics needed to isolate and identify defective bearing axle locations without ambiguity.

The Applicants, after extensive experimentation, have found that placement of the horn assembly is critical so as to avoid picking up excessive background noise (e.g., wheel/rail rubbing; flange/rail squeal; loose equipment or cargo rattling; car-body noise; clacking of rail joints for track circuits). Applicants have found that the horn must not be too far back so as to pick up excessive background noise but must be close enough so as to pick up a signature over a horizontal linear distance corresponding to one circumference or rotation of the wheel in order to capture defect repetition rate signatures that generally repeat once per wheel rotation. A wider range than this causes ambiguous results as the horn may monitor different axles simultaneously. A lesser range than this may result in inadequate information for processing. Furthermore, the horn should not pick up a vertical distance above or below the wheel. Therefore, Applicants have found that a horn elongated in the horizontal plane and shortened in the vertical plane to collect over a wide horizontal angle so as to collect acoustic vibrations from a 120 degree horizontal angle is well adapted to the present purpose.

Additionally, Applicants have found that a horn placed four feet outboard of the rail gage 19, pointing horizontally with its horizontal axis sixteen inches (the mean radius of a 28 inch wheel and a 36 inch wheel) above the rail picks up sound horizontally for about six feet and vertically for about two feet.

A preamp and a lowpass filter are incorporated into the assembly thereby preventing the broad range of background noise from overloading later amplifying and processing means. Additionally, a heater and protective shutter are added to the assembly to prevent ambient weather conditions from either damaging or altering the response of the microphone.

Additionally, for off-site or laboratory work, source 22 could easily be a tape-recorder in a playback mode.

The output of either source 22 may be input into high pass filter 30, or low pass filter 32. Additionally, the user may bypass both filters 30 and 32 by setting switch 33 depending upon the need to filter the electrical signal due to changes in the frequency of interest, ambient acoustic conditions, any radio-frequency or electromagnetic interferences and the like, thereby allowing the maximum dynamic range of the system to be used. Amplifier 34 increased the electrical signal to a usable level. The amplifier 34 preferably has a fixed gain set with no vernier control so as to preclude the possibility of operating in the uncalibrated mode.

The signal is then processed by a high frequency bandpass filter 36. This filter 3 has characteristics which are adjustable by the user in accordance with the frequency of interest. Additionally, the user may bypass filter 36 by use of switch 37.

Envelope detector 38 acts as an amplitude demodulator for the output of the high frequency bandpass filter 36 by rejecting the preselected carrier frequency and passing the positive half of any envelope frequency which may be present. Envelope detector 38 may be bypassed by use of switch 39.

The result of this amplitude demodulation, which may contain envelope frequencies which were modulating the preselected carrier frequencies, is processed by up to twelve parallel low-frequency tuneable bandpass filters 40-51 to remove any signal components which are spurious or not of interest, including any direct current component. The twelve filters correspond to the twelve permutations of four bearing/wheel types (28 inch diameter wheel with a seventy ton capacity, 6"×11" bearing assembly; 33 inch diameter wheel with a seventy ton capacity, 6"×11" bearing assembly; 36 inch diameter wheel with a seventy ton capacity, 6"×11" bearing assembly; and a 36 inch diameter wheel with a one hundred ton capacity, 6½"×12" bearing assembly) and three defect types (bearing assembly roller, cup and cone failures). Each of the twelve band pass filters 40-51 is tuned to a different characteristic impact frequency. The tuning of each of the band-pass filters 40-51 is responsive to a train speed sensor 67. The outputs of band-pass filters 40-51 are monitored by alarm limit monitors 52-63. The alarm limit monitors may be responsive to a number of threshold alarm level values of input amplitude, each corresponding to a different severity of the defect of interest. The threshold alarm level value may be adjusted in response to train speed sensor 67. Additionally, a prior art infrared detection means 65 may be used to detect heat build-up thereby verifying the severity of the bearing defect. As band-pass filters 40-51 have removed any direct current components of the signal, this monitoring must be done in the peak-to-D.C. mode. When an alarm limit monitor 52-63 sensing an input amplitude greater than a threshold value, the monitor 52-63 sends an appropriate message to display means 64. Display means 64 maybe a display or light in a control room, it may include a central processing unit and memory means. Monitors 52-63 may also activate video or photographic means 66 to record the serial number of the passing train. Train speed sensor 67 may also include means for counting the number of railroad cars and/or axles (not shown) which pass, thereby providing means for determining which car has generated the impact frequencies characteristic of a bearing assembly defect.

Figure 3:
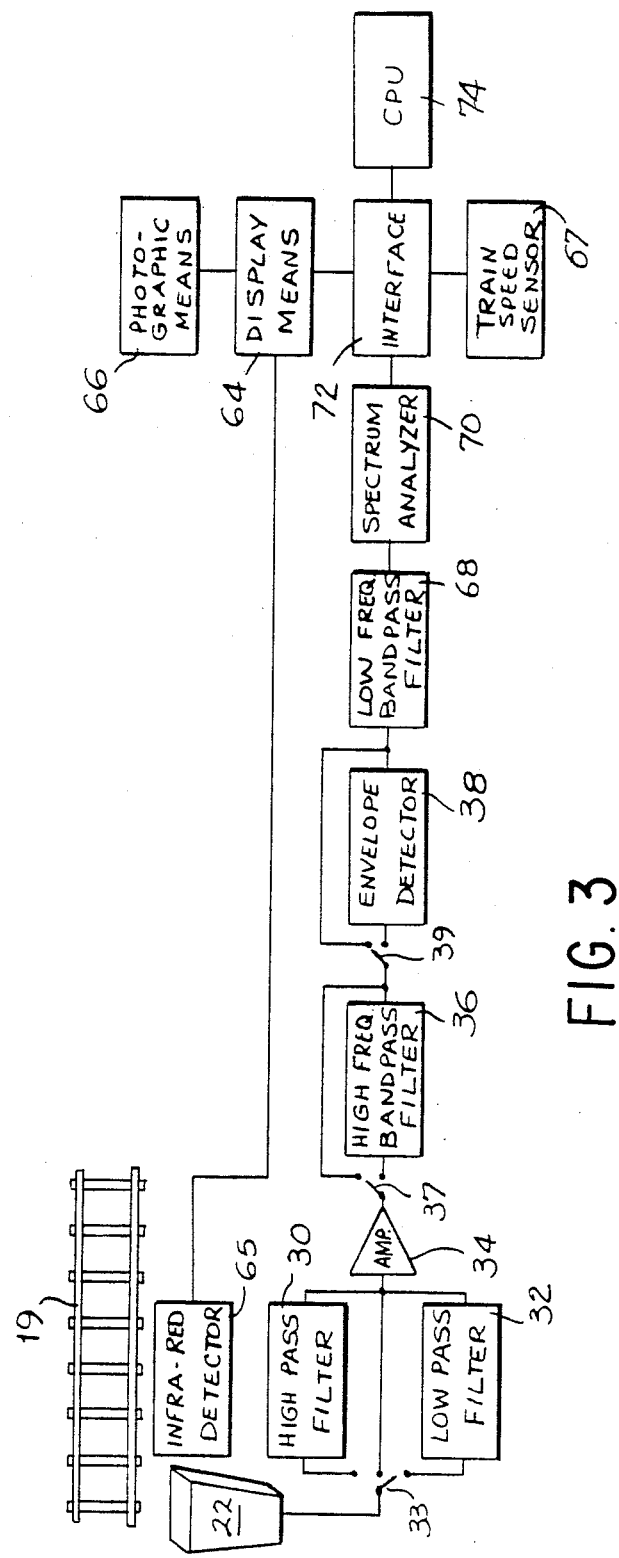
FIG. 3 shows a schematic of an alternative embodiment of this apparatus.

Alternatively, as shown in FIG. 3, band-pass filters 40-51 may be replaced with a single low band-pass filter 68 at a bandwidth (which may be adjustable) broad enough to pass all frequencies of interest to a spectrum analyzer 70, which outputs a digital representation of the frequency domain to a central processing unit (CPU) 74 and associated interfaces 72 which receives an input from the train speed sensor 67, calculates the characteristic impact frequencies, compares them to the output of spectrum analyzer 70 and, upon finding a match therebetween, signals display means 64.

Obviously, numerous modifications may be made to the apparatus without departing from the scope of the invention as defined in the appended claims.

What is claimed is:

1. An apparatus for monitoring bearing assemblies of railroad cars for defects during operation comprising:
   means for transducing acoustic vibrations produced by said assemblies into a first electric signal;
   means for filtering frequency components not substantially equal to a preselected carrier frequency band substantially in the range from 10 to 12 Kilohertz from said first electrical signal, said filtering means having an output;
   means for receiving said filtering means output, demodulating an envelope which modulates said carrier frequency band, and transmitting said envelope, said envelope having frequency components;
   means for receiving said envelope, analyzing said frequency components of said envelope; and
   display means responsive to said analyzing means.

2. The apparatus of claim 1 further including means for amplifying said first electrical signal.

3. The apparatus of claim 2 wherein said amplifying means further includes filtering means.

4. The apparatus of claim 3, wherein said analyzing and receiving means includes at least one bandpass filter.

5. The apparatus of claim 4 wherein said at least one bandpass filter has an adjustable center frequency.

6. The apparatus of claim 5 further including train speed sensing means which automatically adjusts said center frequency.

7. The apparatus of claim 3 wherein said analyzing and receiving means includes a plurality of bandpass filters operating in parallel.

8. The apparatus of claim 7 wherein said plurality of bandpass filters have an adjustable center frequency.

9. The apparatus of claim 3 wherein said analyzing and receiving means includes a spectrum analyzer having a frequency domain output.

10. The apparatus of claim 3 further including bearing speed sensor means and wherein said analyzing and receiving means calculates characteristic impact frequencies responsive to said bearing speed sensor means, and compares said characteristic impact frequencies to said frequency domain output, said display means being responsive to a match found thereby.

11. The apparatus of claim 1 further including infrared sensing means for verifying defect severity of the bearing assembly.

12. The apparatus of claim 1 wherein said transducing means includes an electret microphone.

13. The apparatus of claim 1 wherein said transducing means includes a microphone inside a horn assembly with a cavity acoustically optimized for said carrier frequency band.

14. The apparatus of claim 1 wherein said transducing means includes a microphone inside a horn assembly, said horn assembly being optimized to receive said acoustic vibrations from a 120 degree horizontal angle.

15. The apparatus of claim 1 wherein said transducing means is placed substantially 4 to 5 feet from where the railroad cars pass.

16. The apparatus of claim 1 wherein said transducing means is optimized and placed so as to receive said acoustic vibrations over a horizontal distance corresponding to one revolution of the bearing assembly.

* * * * *